(12) United States Patent
Sato et al.

(10) Patent No.: US 6,274,750 B1
(45) Date of Patent: Aug. 14, 2001

(54) DIMER AND TRIMER ACID ESTERS FROM EPOXIDIZED COMPOUNDS AND METHODS FOR THEIR PREPARATION

(75) Inventors: Setsuo Sato; Ramiro Carielo Bueno, both of Jacarei-SP; Wanderson Bueno De Almeida, S.J. dos Campos-SP, all of (BR)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/119,558

(22) Filed: Jul. 21, 1998

(51) Int. Cl.$^7$ .................................................. C07C 59/00
(52) U.S. Cl. ........................... 554/213; 554/25; 554/149; 554/169; 554/227; 528/295.5; 528/296; 530/211
(58) Field of Search ............................... 554/25, 149, 164, 554/213, 227; 528/295.5, 296; 530/211

Primary Examiner—Deborah D. Carr
(74) Attorney, Agent, or Firm—John E. Drach; Henry E. Millson, Jr.

(57) ABSTRACT

Mixtures of dimeric and trimeric fatty acid $C_{1-4}$ alkyl esters and processes for their preparation comprising either A) epoxidizing an unsaturated or partially hydrogenated fatty acid glyceride;

B) transesterifying the epoxidized glyceride with a $C_{1-4}$ alkanol to obtain epoxidized fatty acid $C_{1-4}$ alkyl esters; and C) ring opening and dimerizing the epoxidized fatty acid $C_{1-4}$ alkyl esters; or A) transesterifying an unsaturated or partially hydrogenated glyceride with a $C_{1-4}$ alkanol to obtain olefinically unsaturated fatty acid $C_{1-4}$ alkyl esters;

B) epoxidizing the unsaturated fatty acid $C_{1-4}$ alkyl esters; and

C) ring opening and dimerizing the epoxidized fatty acid $C_{1-4}$ alkyl esters.

31 Claims, No Drawings

DIMER AND TRIMER ACID ESTERS FROM EPOXIDIZED COMPOUNDS AND METHODS FOR THEIR PREPARATION

FIELD OF THE INVENTION

This invention relates to processes for the preparation of dimer and trimer fatty acid esters.

BACKGROUND OF THE INVENTION

Processes for the preparation of dimeric fatty acids are known to the art.

Dimeric fatty acids are used as Intermediates for the preparation of polyamides useful, inter alia, as a component of ink compositions, adhesives, surface coating materials, and sealants.

SUMMARY OF THE INVENTION

The present invention relates to mixtures of dimeric and trimeric fatty acid $C_{1-4}$ alkyl esters and to processes for their preparation. These mixtures of esters can be used to prepare polyamides that are useful as a component of ink compositions, adhesives, surface coating materials, and sealants.

DETAILED DESCRIPTION OF THE INVENTION

Other than in the operating examples, or where otherwise indicated, all numbers expressing quantities of ingredients or reaction conditions used herein are to be understood as modified in all instances by the term "about".

A first embodiment of the process of the invention comprises the steps of

A) epoxidizing an unsaturated or partially hydrogenated fatty acid glyceride;

B) transesterifying the epoxidized glyceride with a $C_{1-4}$ alkanol to obtain epoxidized fatty acid $C_{1-4}$ alkyl esters; and C) ring opening and dimerizing the epoxidized fatty acid $C_{1-4}$ alkyl esters.

In step A) the glyceride is an unsaturated or partially hydrogenated fatty acid glyceride, which can be a mono-, di- or tri- glyceride, or a mixture of such glycerides, and is preferably predominantly a triglyceride. Natural or synthetic oils having a monounsaturated fatty acid chain or chains, e.g. having a high oleic acid content are preferred. Soybean oil and castor oil are preferred triglyceride oils for use herein. Other useful oils include tall oil, sunflower oil, safflower oil, rapeseed oil, fish oils, vegetable oils, linseed oil, and oiticica oil. The fatty acid chains preferably contain from 8 to 24 carbon atoms, more preferably from 12 to 18 carbon atoms.

Step A) is carried out using a peracid or combination of peracids, such as hydrogen peroxide or an organic peroxide, e.g. performic acid, or an inorganic peroxide such as sodium or potassium peroxide. Hydrogen peroxide and/or performic acid is preferred.

The step A) reaction temperature can range from 20° C. to 100° C., preferably from 60 to 75° C. The glycerides are reacted until all unsaturated chains have at least one epoxy group. Preferably the oxirane content should be in the range of from 4.0 to 6.0% with an iodine value of from 4 to 70, and preferably less than 30.0.

When hydrogen peroxide is used in step A), an aqueous solution of from 50 to 70% $H_2O_2$ is preferred. Also preferred is to carry out this step in the presence of formic acid, acetophosphonic acid, and phosphoric acid, in addition to the hydrogen peroxide.

Moreover, useful epoxidized oils including epoxidized soybean oil are commercially available, and they can be used if desired in the process of the invention, thus eliminating the need for step A) of the process.

Step B) is carried out by reacting the epoxidized glyceride with a $C_{1-4}$ alkanol, preferably methanol, although ethanol, propanol, isopropyl alcohol, n-butanol, or isobutyl alcohol can also be used. The reaction is preferably carried out at a temperature in the range of from 25° to 85° C., more preferably in the range of from 35 to 55° C. in the presence of an effective quantity of a catalyst. Any catalyst useful in carrying out transesterification reactions can be employed, such as sodium methoxide or zinc oxide, provided the catalyst does not cause opening of the epoxy groups.

The ratio by weight of $C_{1-4}$ alkanol to epoxidized glyceride is from 1:1 to 0.25:1, preferably from 0.75:1 to 0.4:1, and more preferably from 0.5:1 to 0.6:1. The catalyst can be present in from 0.05% to 5%, preferably from 0.1 to 4% by weight, based on the weight of the epoxidized glyceride.

Step C) is carried out by reacting the epoxidized fatty acid $C_{1-4}$ alkyl esters from step B) in the presence of a ring opening agent at a temperature in the range of from 25 to 115° C., preferably from 40 to 115° C. It is preferred to use approximately molar quantities of ring opening agents based on oxirane groups.

The ring opening agents that can be used in step C) alone or in combination include phosphoric acid, phosphorous acid, hypophosphorous acid, phosphorus trichloride, monoalkyl phosphates, e.g. methylphosphoric acid and butyl hydrogen phosphate, boron halides, boric acid, boronic acids, e.g. R (B) $OH_2$ where R is a $C_{1-6}$ alkyl group, disulfonic acids, phosphonic acids, e.g. derivatives of the hypothetical phosphonic acid $(HP(O)(OH)_2)$ such as acetophosphonic acid or $RPO(OH)_2$ where R can be an alkyl or aromatic hydrocarbon group, phosphonamides, i.e. amides of the above phosphonic acid derivatives, polybasic carboxylic acids, e.g. malonic, succinic, glutaric, adysic, sebacic, fumaric, phthalic and isophthalic acids, and hydroxycarboxylic acids, e.g. glycolic, hydroxymalonic, citric, and tartaric acids.

Optionally, a polyhydroxy-substituted alkane can also be present in the step C) reaction mixture. Polyhydroxy-substituted alkanes that can be used herein include alkylene glycols, e.g. ethylene glycol, propylene glycol, and 1,4-butane diol, trimethylol propane, pentaerythritol, and the like. The polyhydroxy alkane can be used in a quantity ranging from 0.1 to 5 moles, preferably from 0.2 to 0.5 moles of hydroxyl group per mole of oxirane group in the epoxidized fatty acid $C_{1-4}$ alkyl ester.

The step C) reaction will produce a reaction mixture containing predominantly dimers, with smaller quantities of trimers. In addition, quantities of higher oligomers and monomers may also be present.

The reaction mixture from step C) containing the dimeric and trimeric fatty acid $C_{1-4}$ alkyl esters can then be reacted with at least one polyamine at a temperature in the range of from 125 to 250° C., preferably from 150 to 225° C. to produce polyamides. The reaction proceeds well in the absence of any catalyst. The polyamines can be alkylene diamines, alkylene triamines, alkylene tetraamines, alkylene pentamines, and alkylene hexamines, e.g. ethylenediamine, diethylenetriamine, triethylenetetraamine, and pentaethylenehexamine. Generally, where the polyamides are to be used as curing agents for epoxy resins, an excess of polyamine is used. Where the polyamides are to be used as ink resins, approximately stoichiometric quantities of the ester and amine functionality are employed.

A second embodiment of the process of the invention comprises the steps of

A) transesterifying an unsaturated or partially hydrogenated glyceride with a $C_{1-4}$ alkanol to obtain olefinically unsaturated fatty acid $C_{1-4}$ alkyl esters;

B) epoxidizing the unsaturated fatty acid $C_{1-4}$ alkyl esters; and

C) ring opening and dimerizing the epoxidized fatty acid $C_{1-4}$ alkyl esters.

In step A) the glyceride is identical to the glycerides used in step A) of the first embodiment of the invention.

Step A) of this second embodiment can be carried out at a temperature in the range of from 25 to 250° C., preferably from 175 to 210° C., and more preferably from 180 to 200° C. with stirring in pressure equipment such as an autoclave for a period of from 1 to 5 hours, preferably from 1.5 to 2.5 hours, depending on the reaction temperature. Reaction pressures can range from 200 to 500 psig, preferably from 300 to 350 psig.

Step B) can be carried out in the same manner as given above for step A) of the first embodiment, i.e. by the use of a peracid.

Step C) of this second embodiment is carried out in the same manner as step C) of the first embodiment.

The reaction mixture from step C) can then be reacted with polyamines to produce polyamides.

The processes of the invention have a number of advantages over known methods for producing dimers and trimers useful for reaction with polyamines.

Such advantages include

1. Depending on the ring opening agent used for reacting with the epoxidized compound, hydroxyl groups or other polar groups can be formed upon ring opening, generating polar sites which can change the physical and chemical properties of the dimer/trimer mixtures and hence the properties of the polyamides prepared therefrom, such as their solubility, stability, reactivity, and the like.

2. The ring opening/dimerization/trimerization reaction is rapid and can be carried out at low temperatures without the need for a catalyst or special equipment.

3. The yields are high and are mainly limited by the number of saturated fatty chains in the glycerides.

4. The molecular weight of the mixture of dimers and trimers can be made higher, if desired, by increasing the presence of oligomers generated from fatty chains having two or three epoxy groups.

5. The processes are less expensive to operate than prior processes. For example, the reaction mixture from step C) can be reacted with polyamines in the same reactor used for step C).

The invention will be illustrated but not limited by the following examples.

EXAMPLES

Example 1

980 Kgs. of refined soybean oil were added to a reactor. 1.7 Kgs. of acetophosphonic acid and 7 kgs. of 85% phosphoric acid were then added with mixing. The mixture was heated to 60° C. and 52 kgs. of 90% formic acid and 260 kgs of 70% $H_2O_2$ were added with mixing over the course of 3 hours, while maintaining the temperature in the reactor at 67–68° C. Then the resulting mixture was mixed at 68–69° C. for an additional period of 1.5 hours until the iodine value fell to less than 30.0. Mixing was discontinued, resulting in an aqueous phase and an organic phase. The aqueous phase was removed and the organic phase was stirred and washed with 200 kgs. of water. The wash water was then separated off, and the organic phase dried under vacuum at 120° C. The organic phase was then filtered in a press filter. The resulting partially epoxidized soybean oil had an acid value of 0.5 mg KOH/gram of epoxidized soybean oil, an iodine value of 25, and an oxirane value of 4.7%.

Example 2

1000 Grams of the partially epoxidized soybean oil prepared in Example 1 was heated to 40° C. with 102 g. of methanol and 20 grams of sodium methoxide under substantially anhydrous conditions (water content no greater than 1500 ppm). Heating with stirring was continued for two hours. Then 50 g. of 6% aqueous $H_3PO_4$ was added, and after 5 minutes stirring was discontinued and the aqueous phase separated from the organic phase. The organic phase was then dried under vacuum at 100° C. until the water content was below 1000 ppm. The epoxidized fatty acid methyl esters had an oxirane content of 4.7%, an acid number of 3.0, a saponification number of 180, a free glycerol content of 0.05%, and a total glycerol content of 1.4%.

Example 3

1000 Grams of epoxidized fatty acid methyl esters, prepared from an epoxidized soybean oil according to the process of Example 2, was added to a reactor, and 82 grams of 98% $H_3PO_4$ (0.8 mols) was added thereto with stirring over the course of 30 minutes while maintaining a temperature of 50° C. Since the reaction is exothermic, the reactor was cooled to maintain the 50° C. temperature. Then the mixture was heated to 100° C. and maintained at this temperature for 20 minutes. The reaction mixture was cooled and analyzed. The mixture had an acid number of 4.0, an oxirane value of 0, a Gardner color of 3, and contained 41.5% of a mixture of dimerized fatty acid methyl esters and trimerized fatty acid methyl esters, 27.2% of higher oligomers, 12.6% of free fatty acid methyl esters, and 18.7% of monomeric hydroxy compounds. The above percentages are by weight.

Example 4

1000 Grams of epoxidized fatty acid methyl esters containing 3.87 mols of oxirane groups prepared according to the process of Example 2 from an epoxidized soybean oil was added to a stirred reactor. 82 Grams of 98% $H_3PO_3$ (0.9 mols) was added with stirring over a period of 30 minutes while maintaining a reaction temperature of 50° C. by cooling. The resulting mixture was then heated to 150° C. and maintained for 30 minutes at this temperature. The reaction mixture was then cooled and analyzed. The mixture had an acid number of 56.0, an oxirane value of 0, a Gardner color of 3, and contained, by weight, 41.2% of a mixture of dimerized fatty acid methyl esters and trimerized fatty acid methyl esters, 19.4% of higher oligomers, 7.7% of free fatty acid methyl esters, and 31.3% of monomeric hydroxy compounds.

Example 5

1000 Grams of epoxidized fatty acid methyl esters containing 2.9 mols of oxirane groups prepared according to the process of Example 2 from an epoxidized soybean oil was added to a reactor. 83 Grams (0.11 mols) of 50% $H_3PO_2$ was added with stirring while maintaining a temperature of 50° C. by cooling. The mixture was then heated to 150° C. and maintained for 60 minutes at this temperature. The mixture was then cooled and analyzed. The mixture had an acid number of 38.0, an oxirane value of 0.3, a Gardner color of 2, and contained, by weight, 42.9% of a mixture of dimerized and trimerized fatty acid methyl esters, 18.4% higher oligomers, 9.2% free fatty acid methyl esters, and 29.1% of monomeric hydroxy compounds.

Example 6

1000 Grams of epoxidized fatty acid methyl esters containing 3.87 mols of oxirane groups prepared according to the process of Example 2 from an epoxidized soybean oil was added to a reactor. 118 Grams (0.86 mols) of PCl$_3$ was added with stirring while maintaining a temperature of 50° C. by cooling. The mixture was then heated to 130° C. and maintained for 30 minutes at this temperature. The mixture was cooled and analyzed. The mixture had an acid number of 11.0, an oxirane value of 0, a Gardner color of 3, and contained, by weight, 33% of a mixture of dimerized and trimerized fatty acid methyl esters, 34% of higher oligomers, 8.4% free fatty acid methyl esters, and 24.3% of monomeric hydroxy compounds.

Example 7

1000 Grams of epoxidized fatty acid methyl esters containing 3.87 mols of oxirane groups prepared according to the process of Example 2 from epoxidized soybean oil and 92 grams (1.48 mols) of ethylene glycol were added to a stirred reactor. 0.4 Grams of 25% trifluoromethane sulfonic acid was added with stirring while maintaining a temperature of 80° C. by cooling. The mixture was then heated to 100° C. over a period of 1 hour, and then maintained at this temperature for an additional hour.

Example 8

580 Grams of the reaction product of Example 3, 326.9 grams of triethylenetetramine, 93 g of tall oil fatty acid, and 0.1 g of monosodium phosphate were added to a reactor. With stirring and under a nitrogen atmosphere, the mixture was heated to 225° C. over a period of 2–3 hours. When the temperature reached 225° C., the nitrogen flow was stopped and a vacuum of 60 mm Hg was applied and held for 2 hours at 225° C. The vacuum was then broken with nitrogen and the polyamide product cooled. The polyamide had an amine value of 336, an acid value of 22.7, and a viscosity at 25° C. of 45,000 cps.

This example shows how polyamides can be prepared from the mixture of dimers and trimers obtained by the process of the invention.

Example 9

681.8 grams of the reaction product of Example 7, and 318.2 grams of triethylenetetramine were added to a reactor. With stirring and under a nitrogen atmosphere, the mixture was heated to 225° C. over a period of 2–3 hours. When the temperature reached 225° C., the nitrogen flow was stopped and a vacuum of 60mm Hg was applied and held for 2 hours at 225° C. The vacuum was then broken with nitrogen and the polyamide product cooled. The polyamide had an amine value of 352, an acid value of 1.8, and a viscosity at 25° C. of 44,000 cps.

This example further illustrates the preparation of polyamides from the mixture of dimers and trimers obtained by the process of the invention.

What is claimed is:

1. A process for the preparation of a mixture of dimeric and trimeric fatty acid $C_{1-4}$ alkyl esters comprising the steps of A) epoxidizing an unsaturated or partially hydrogenated unsaturated fatty acid glyceride;

B) transesterifying the epoxidized fatty acid glyceride with a $C_{1-4}$ alkanol to obtain epoxidized fatty acid $C_{1-4}$ alkyl esters; and C) dimerizing the epoxidized fatty acid $C_{1-4}$ alkyl esters.

2. The process of claim 1 in which in step A) the fatty acid glyceride is a natural oil.

3. The process of claim 2 wherein the natural oil is soybean oil or castor oil.

4. The process of claim 1 wherein in step A) a peracid is used as the epoxidizing agent.

5. The process of claim 1 wherein step B) is carried out at a temperature of from about 25° to about 85° C. in the presence of a transesterification catalyst.

6. The process of claim 5 wherein the transesterification catalyst is sodium methoxide.

7. The process claim 1 wherein in step B) the $C_{1-4}$ alkanol is methanol.

8. The process of claim 1 wherein step C) is carried out by use of a ring opening agent.

9. The process of claim 8 wherein step C) is carried out at a temperature in the range of from about 25 to about 115° C.

10. The process of claim 8 wherein the ring opening agent is phosphoric acid, phosphorous acid, hypophosphorous acid, or phosphorus trichloride.

11. The process of claim 1 wherein in step C) a polyhydroxy-substituted alkane is present as a reactant.

12. The process of claim 1 wherein in step C) a mixture comprising both dimeric and trimeric fatty acid $C_{1-4}$ alkyl esters is obtained.

13. The process of claim 1 wherein in step A) the fatty acid glyceride is a natural oil, in step B) a transesterification catalyst is present and the $C_{1-4}$ alkanol is methanol, and step C) is carried out by use of a ring opening agent.

14. A process for the preparation of a mixture of dimeric and trimeric fatty acid $C_{1-4}$ alkyl esters comprising the steps of I) transesterifying an epoxidized fatty acid glyceride with a $C_{1-4}$ alkanol to obtain epoxidized fatty acid $C_{1-4}$ alkyl esters; and II) dimerizing the epoxidized fatty acid $C_{1-4}$ alkyl esters.

15. The process of claim 14 in which in step I) the epoxidized fatty acid glyceride is derived from a natural oil.

16. The process of claim 14 wherein step II) is carried out by use of a ring opening agent.

17. A process for the preparation of a mixture of dimeric and trimeric fatty acid $C_{1-4}$ alkyl esters comprising the steps of A) transesterifying an unsaturated or partially hydrogenated glyceride with a $C_{1-4}$ alkanol to obtain olefinically unsaturated fatty acid $C_{1-4}$ alkyl esters;

B) epoxidizing the unsaturated fatty acid $C_{1-4}$ alkyl esters; and

C) dimerizing the epoxidized fatty acid $C_{1-4}$ alkyl esters.

18. The process of claim 17 wherein in step A) the glyceride is a natural oil.

19. The process of claim 18 wherein the natural oil is soybean oil or castor oil.

20. The process of claim 17 wherein in step B) a peracid is used as the epoxidizing agent.

21. The process of claim 17 wherein step A) is carried out at a temperature in the range of from 25 to 250° C. in the presence of a transesterification catalyst.

22. The process of claim 21 wherein the transesterification catalyst is sodium methoxide and the temperature is in the range of from about 25° to about 85° C.

23. The process of claim 17 wherein in step A) the $C_{1-4}$ alkanol is methanol.

24. The process of claim 17 wherein step C) is carried out by use of a ring opening agent.

25. The process of claim 24 wherein step C) is carried out at a temperature in the range of from about 25 to about 115° C.

26. The process of claim 24 wherein the ring opening agent is phosphoric acid, phosphorous acid, hypophosphorous acid, or phosphorus trichloride.

27. The process of claim 17 wherein in step C) a polyhydroxy-substituted alkane is present as a reactant.

28. The process of claim 17 wherein in step C) a mixture comprising both dimeric and trimeric fatty acid $C_{1-4}$ alkyl esters is obtained.

29. The process of claim 17 wherein in step A) the fatty acid glyceride is a natural oil, a transesterification catalyst is present, and the $C_{1-4}$ alkanol is methanol, and step C) is carried out by use of a ring opening agent.

30. The mixture of dimeric and trimeric fatty acid $C_{1-4}$ alkyl esters obtained by the process of claim 1.

31. The mixture of dimeric and trimeric fatty acid $C_{1-4}$ alkyl esters obtained by the process of claim 17.

* * * * *